(12) United States Patent
Mizoguchi et al.

(10) Patent No.: US 11,328,048 B2
(45) Date of Patent: May 10, 2022

(54) METHOD FOR LOGGING IN TO SYSTEM

(71) Applicant: Satoshi Mizoguchi, Tokyo (JP)

(72) Inventors: Satoshi Mizoguchi, Tokyo (JP); Masao Kishikawa, Tokyo (JP); Mariko Mizoguchi, Tokyo (JP)

(73) Assignee: Satoshi Mizoguchi, Tokyo (JP)

( * ) Notice: Subject to any disclaimer, the term of this patent is extended or adjusted under 35 U.S.C. 154(b) by 426 days.

(21) Appl. No.: 16/691,874

(22) Filed: Nov. 22, 2019

(65) Prior Publication Data

US 2020/0089864 A1 Mar. 19, 2020

Related U.S. Application Data

(63) Continuation of application No. PCT/JP2018/021596, filed on Jun. 5, 2018.

(30) Foreign Application Priority Data

Jun. 8, 2017 (JP) .............................. JP2017-113065

(51) Int. Cl.
*G06F 21/36* (2013.01)
*G16H 10/60* (2018.01)
*G06K 19/06* (2006.01)

(52) U.S. Cl.
CPC ....... *G06F 21/36* (2013.01); *G06K 19/06037* (2013.01); *G16H 10/60* (2018.01)

(58) Field of Classification Search
CPC ... G06F 21/36; G06F 13/00; G06K 19/06037; G16H 10/60; G06Q 50/22
USPC ........................................................ 726/19
See application file for complete search history.

(56) References Cited

U.S. PATENT DOCUMENTS

| | | | | |
|---|---|---|---|---|
| 10,296,716 B1* | 5/2019 | Skocic | ..................... | G06F 16/13 |
| 10,410,308 B2* | 9/2019 | Abousy | ..................... | G16H 10/60 |
| 10,600,508 B1* | 3/2020 | Allen | ....................... | G16H 10/60 |
| 10,897,461 B2* | 1/2021 | Schwartz | ................ | H04L 63/08 |
| 10,971,251 B1* | 4/2021 | Giobbi | .................... | G06Q 10/10 |

(Continued)

FOREIGN PATENT DOCUMENTS

| | | | |
|---|---|---|---|
| JP | 2003076789 A | 3/2003 |
| JP | 2006184980 A | 7/2006 |

(Continued)

OTHER PUBLICATIONS

International Search Report for International Application No. PCT/JP2018/021596, dated Sep. 4, 2018.

*Primary Examiner* — Jeffrey C Pwu
*Assistant Examiner* — Nega Woldemariam
(74) *Attorney, Agent, or Firm* — The Marbury Law Group, PLLC

(57) ABSTRACT

A method for logging in to a system is provided in which a mobile terminal is provided with a function to create a high-density two-dimensional code, access information for accessing an electronic chart system and a time stamp are recorded in the high-density two-dimensional code, the high-density two-dimensional code is deformed, generated and displayed in synchronism with time information of the time stamp, and a high-density two-dimensional code generated by a high-density two-dimensional code authentication read scanner is read, whereby logging in to the electronic chart system becomes possible while taking security into consideration.

5 Claims, 4 Drawing Sheets

(56) References Cited

U.S. PATENT DOCUMENTS

| | | | | |
|---|---|---|---|---|
| 2004/0128163 A1* | 7/2004 | Goodman | ............... | G16H 10/60 |
| | | | | 705/2 |
| 2012/0138679 A1 | 6/2012 | Doyle | | |
| 2015/0205919 A1* | 7/2015 | Robertson | ............... | G16Z 99/00 |
| | | | | 705/3 |
| 2016/0019353 A1* | 1/2016 | Cavagnaro | ............... | H04W 4/90 |
| | | | | 705/3 |
| 2016/0027138 A1* | 1/2016 | Larsen | ................ | G16H 10/60 |
| | | | | 705/2 |
| 2016/0042483 A1* | 2/2016 | Vo | ........................ | G16H 10/60 |
| | | | | 705/3 |
| 2016/0371459 A1* | 12/2016 | Minemura | ......... | G06Q 30/0633 |
| 2017/0006146 A1* | 1/2017 | Homma | ................ | H04L 67/04 |
| 2017/0068784 A1* | 3/2017 | Sullivan | ................ | G16H 10/60 |

FOREIGN PATENT DOCUMENTS

| | | | |
|---|---|---|---|
| JP | 2007080289 A | 3/2007 | |
| JP | 3921489 B2 | 5/2007 | |
| JP | 2014092831 A | 5/2014 | |
| JP | 2016195396 A | 11/2016 | |

\* cited by examiner

SPECIFICATION AND CONFIGURATION
OF RECEPTION PC

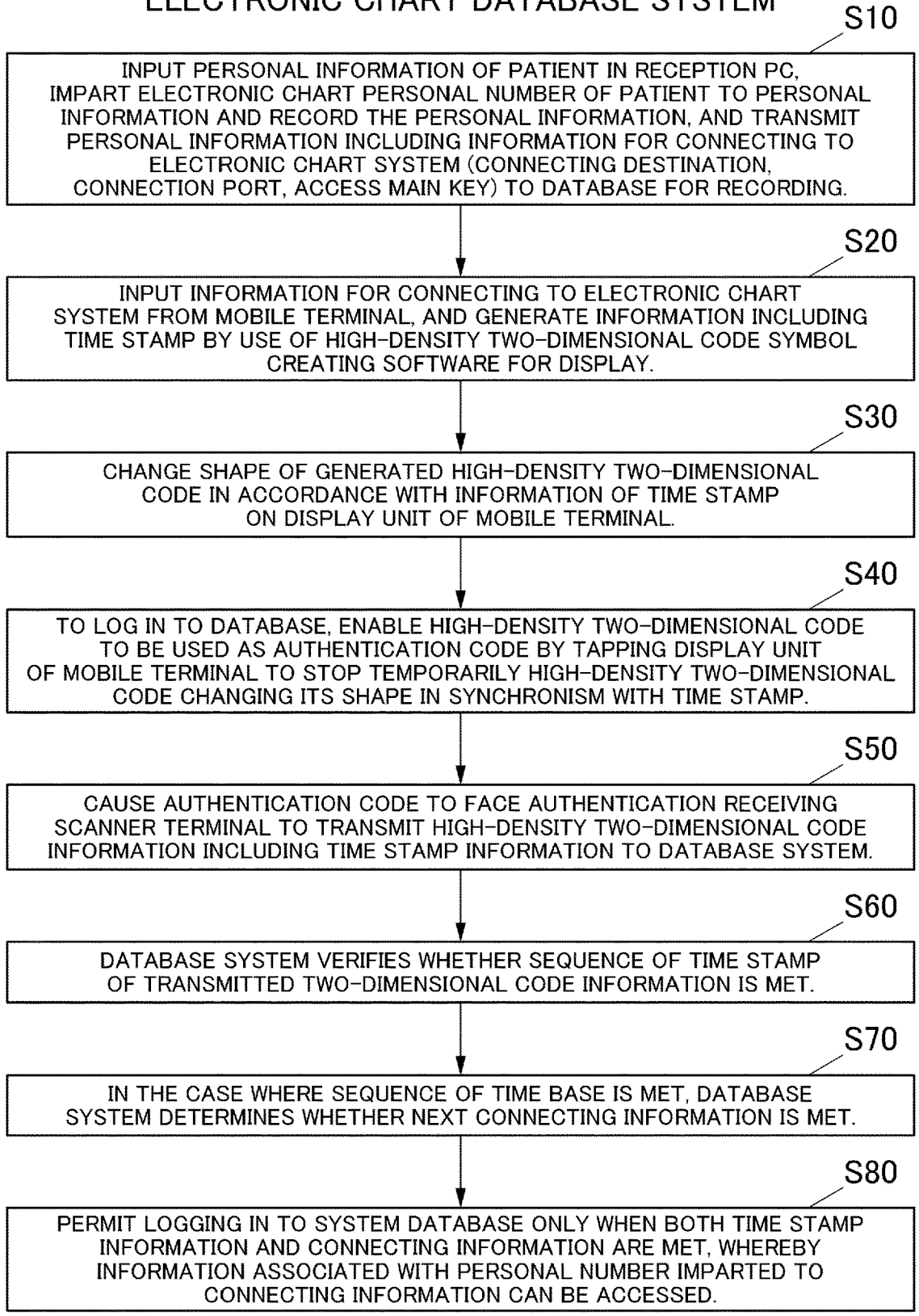

METHOD FOR LOGGING IN TO SYSTEM

CROSS-REFERENCE TO RELATED APPLICATION

This application is based upon and claims the benefit of priority under 35 USC 119 of PCT Application No. PCT/JP2018/021596 filed on Jun. 5, 2018, the entire disclosure of which, including the description, claims, drawings, and abstract, is incorporated herein by reference in its entirety.

BACKGROUND OF THE INVENTION

Field of the Invention

The present invention relates to a system for logging in to an electronic chart system where medical information regarding clinical actions is electronically processed by use of a computer for use over a medical network by making use of a mobile terminal.

Description of the Related Art

An electronic chart constitutes a system in which a paper chart on which a doctor normally writes the history of clinical actions taken by the doctor is replaced with an electronic system, the chart is edited and managed altogether as electronic information, and the chart is recoded in a database, or means recording the electronic information in the database.

Introducing a high-quality electronic chart system contributes to improving the work efficiency and helping to reduce the work staff and the running costs, as well as overtime work. As a result, the environment of a clinical site is improved, whereby an improvement in individual motivation of those who work there can be expected. Additionally, the introduction is effective in increasing the reliability and evaluation of a hospital, the number of patients to visit the hospital, and the like, whereby the management of the hospital can be improved. Further, the high-quality electronic chart system can strongly support a future expansion of the hospital in terms of size both physically and mentally.

However, personal information and clinical information of a patient who is treated constitute highly privacy information. Thus, in order to prevent the leakage of such information due to infection by computer viruses or unauthorized computer access, security against them needs to be taken into consideration. Additionally, there can be generated a risk of a large quantity of data being stolen within a short period of time.

As one of such countermeasures, a person authentication is considered to confirm for sure whether a person who wants to access the electronic chart system is the doctor who writes the chart. Then, Japanese Patent Laid-Open No. 2003-76789 discloses an electronic chart system in which such a person authentication is performed. The electronic chart system disclosed in this patent literature is a system in which an information system transfers an electronic chart based on a transfer instruction from a card-loaded mobile phone, and a person authentication is performed based on card information and a password that are transmitted from the mobile phone to the information system.

However, since the mobile phone includes no means for registering the card information and the password which are used for the person authentication in the information system, the user needs to perform troublesome registration work such as visiting a predetermined reception place, for example.

In addition, in the case of authentication by making use of knowledge information that makes use of a user name and a password, since this type of authentication can be introduced easily and at low cost, it is a merit of this type of authentication that various systems can be made use of relatively easily. On the other hand, it is a demerit of this type of authentication that security can be an issue. To deal with the issue, passwords are changed periodically, or a long password is set to enhance the security. However, there are reported cases where the user cannot memorize the password itself, as a result of which the user writes down the long password and eventually encounters a crime of a social engineering.

Additionally, there is caused a problem in that it takes some time to perform authentication at a place where a communication environment is not good.

The two-dimensional code compression technique and symbol design that were developed in 1980s in the United States of America have also been improved. For example, since the high-density two-dimensional code described in Japanese Patent Application No. 2016-195396 can record information highly densely, multi-language voice information can also be recorded.

SUMMARY OF THE INVENTION

An object of the invention is to provide a method for logging in to a system while securing the conventional personal privacy information described above and preventing the leakage of information.

According to an aspect of the present invention, there is provided a method for logging in to a system, wherein a reception PC receives patient's personal information that is inputted from an input unit, embeds information for connecting to a system server (a connecting destination, a connection port, a main access key) in the personal information, records the resulting personal information in a recording unit, and transmits the personal information to an electronic chart system to be recorded therein.

A mobile terminal imparts embeds a time stamp in information for connecting to the electronic chart system (a connecting destination, a connection port, a main access key) to thereby generate a high-density two-dimensional code and displays the high-density two-dimensional code generated on a display unit, and the high-density two-dimensional code displayed on the display unit of the mobile terminal continues to change its shape until the high-density two-dimensional code is stopped continuing its shape at a time corresponding to a time of the time stamp.

The high-density two-dimensional code can be used as an authentication two-dimensional code by stopping temporarily the display of the high-density two-dimensional code on the mobile terminal.

The authentication two-dimensional code is read by a high-density two-dimensional code authentication read scanner and is transmitted to the electronic chart system.

The authentication code information read in the way described above is determined whether the authentication code information is true or false by verifying a sequence of the time stamp in the electronic chart system.

The information for connecting to the system (a connecting destination, a connection port, a main access key) is verified after the verification of the time stamp, and the personal information can be outputted only when the connecting information matches information that is recorded in advance.

According to the method for logging in to a system of the present invention, the time stamp is embedded in the information recorded on the high-density two-dimensional code to generate a symbol, and hence, every time a symbol is generated, the shape of the information changes, whereby the method for logging in to a system can be provided which is effective in preventing the leakage of information that would otherwise be realized by imaging and copying the symbol.

BRIEF DESCRIPTION OF THE SEVERAL VIEWS OF THE DRAWINGS

FIG. 4 is a flowchart of a method for logging in to an electronic chart system.

DETAILED DESCRIPTION OF THE PREFERRED EMBODIMENT

Figure 1:
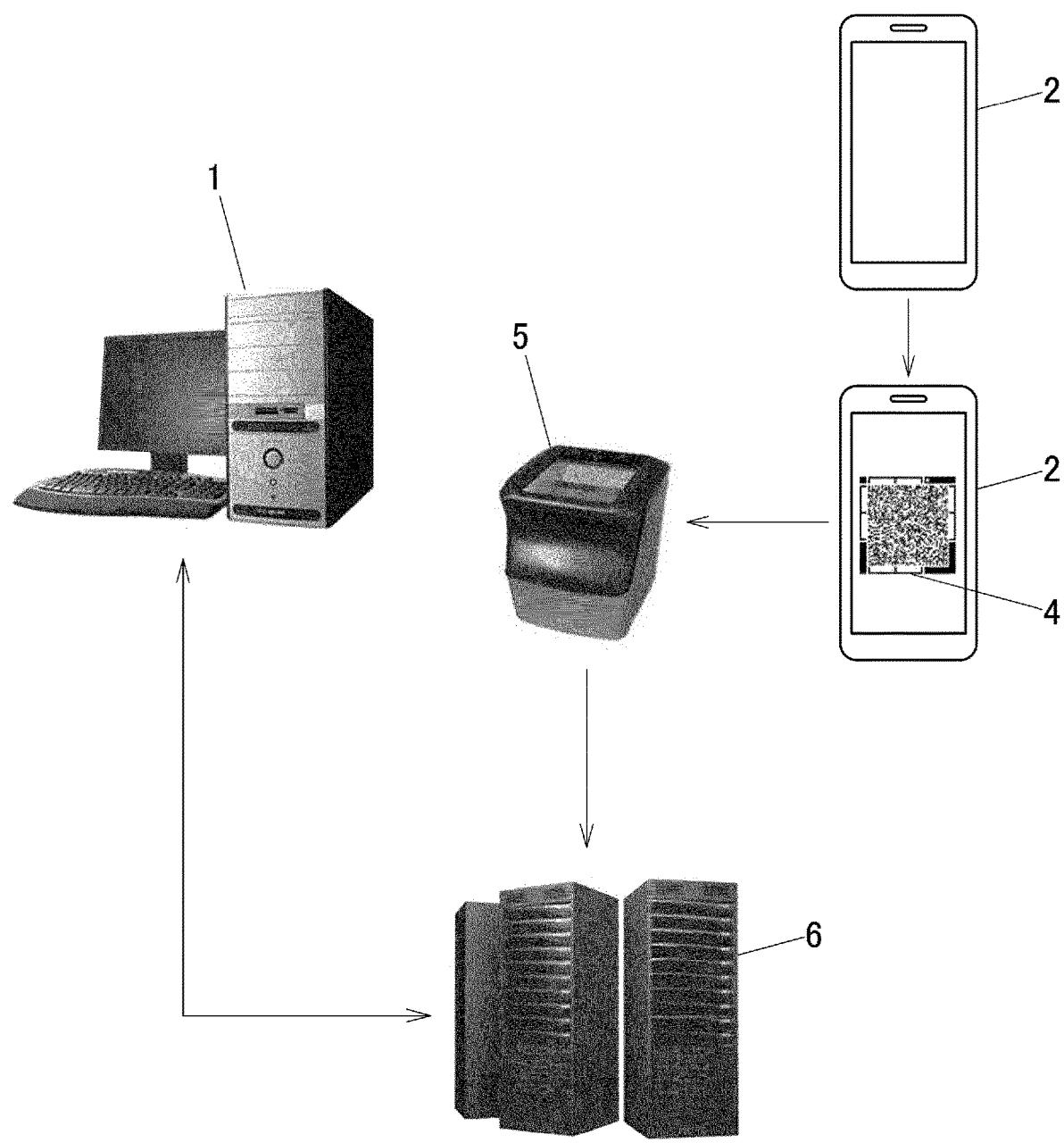
FIG. 1 is a schematic block diagram of a system according to the present invention.

An embodiment of an invention according to claims will be described with reference to FIGS. 1 to 4. FIG. 1 is a schematic block diagram illustrating a reception PC 1, a mobile terminal 2, and an electronic chart system 6 according to the embodiment.

Figure 3:
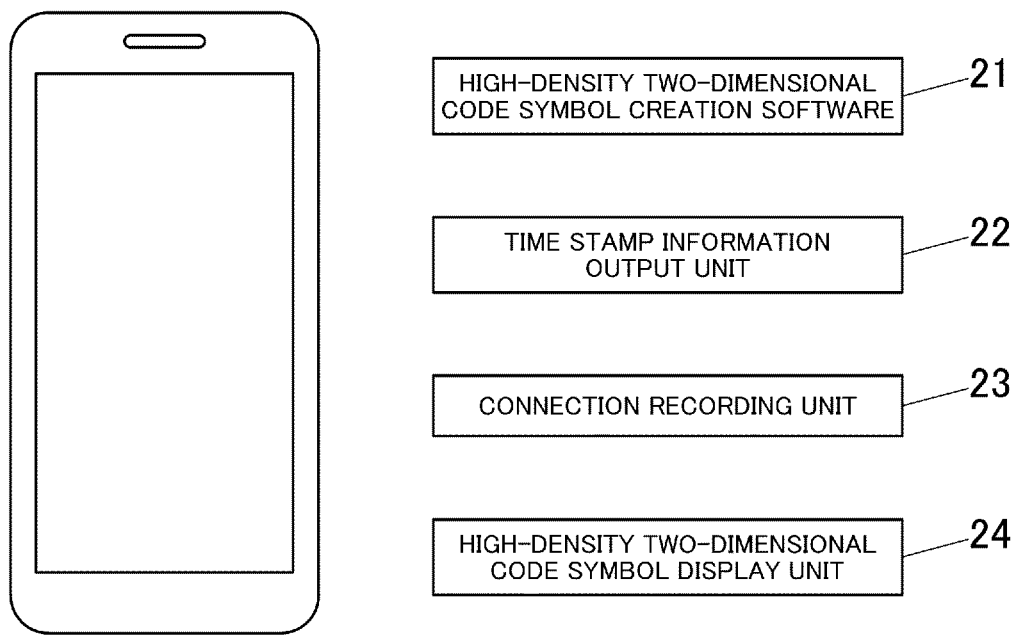
FIG. 3 is a schematic block of a specification and a configuration of a mobile terminal.

As illustrated in FIG. 3, the mobile terminal 2 includes high-density two-dimensional code symbol creation software 21, a time stamp information output unit 22, a connection recording unit 23, and a high-density two-dimensional code symbol display unit 24.

Figure 2:
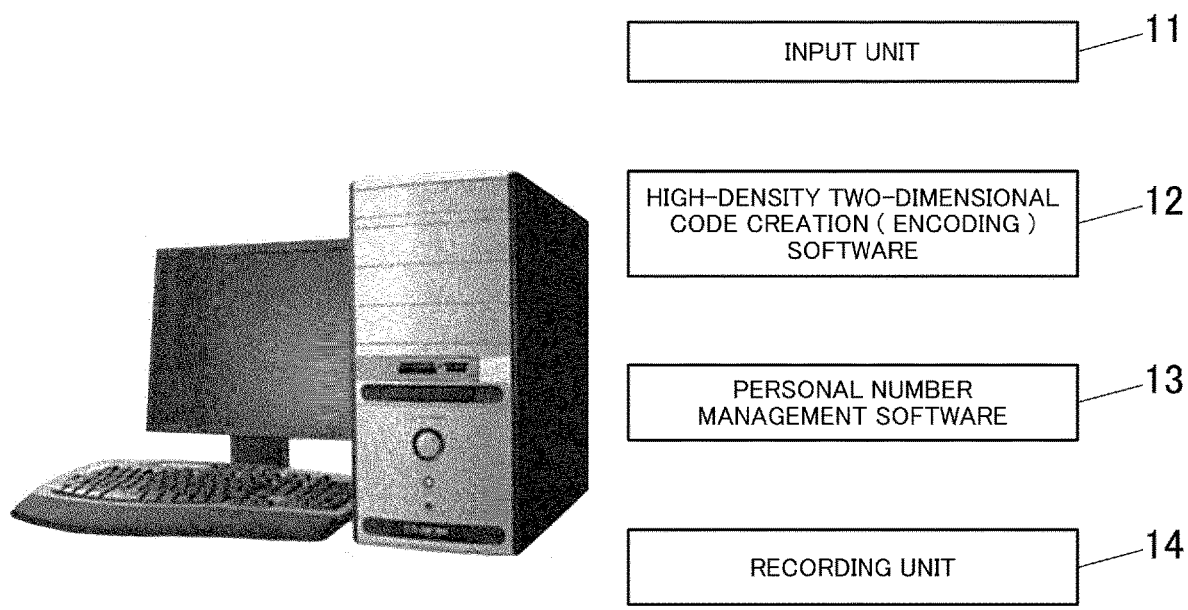
FIG. 2 is a schematic block diagram of a specification and a configuration of a reception PC.

The reception PC1, which is a reception device, includes an input unit 11 for inputting patient's personal information and a recording unit 14, as shown in FIG. 2. High-density two-dimensional code creation (encoding) software 12 and personal number management software 13 are recorded in the recording unit 14 of the reception PC 1. The reception PC 1 includes additionally an information transmission unit (not shown) for outputting patient's personal information in association with a personal number on an electronic chart.

Next, a method for logging in to the electronic chart system 6 shown in FIG. 4 will be described. Firstly, at step S10, a user such as a doctor inputs patient's personal information through the input unit 11 of the reception PC 1 and gives a patient a personal number on his or her electronic chart, whereby the reception PC 1 records the personal number and the personal information of the patient in association with each other in the recording unit 14 therein.

The personal information of a patient includes address, name, contact telephone number, type of health insurance, health insurance card number, medical history (hypertension, diabetes, cancer myocardial infarction, cerebral infarction, and the like), nursing care insurance (the aged), allergy, tobacco, alcohol, family history (history of dieses or the like), and these pieces of information are all tagged.

Next, at step S20, the mobile terminal 2 creates information for connecting to the electronic chart system 6 (a connecting destination, a connection port, a main access key), as well as a high-density two-dimensional code 4 including a time stamp embedded at the time of creating a symbol using the symbol creation software 21. The connecting destination and the contact port constitute connecting information with which the reception PC 1 specifies a connection method to the electronic chart system 6. Authentication information such as a user name, a user ID, a user password, and the like can arbitrarily be included in the main key, which is authentication information. The high-density two-dimensional code 4 is specialized in logging in to the electronic chart system 6, and a header structure of a header section of the main key is modified and encrypted so as to be decrypted by the reception PC 1.

Timing information for the high-density two-dimensional code 4 is also additionally recorded together with the time stamp embedded at the time of creating the symbol in the high-density two-dimensional code 4.

The timing information for the high-density two-dimensional code 4 means an effective time limit for the high-density two-dimensional code. In the case where the timing information is a timing symbol that is set to be effective for 30 minutes from the time of creating the symbol, it is programmed that the high-density two-dimensional code 4 is stopped being displayed after 30 minutes have elapsed and that the various pieces of information recorded in the reception PC 1 become ineffective.

At step S20, the high-density two-dimensional code 4 that is generated as illustrated in FIG. 1 is displayed on the mobile terminal 2. An updating time for display of the high-density two-dimensional code 4 can be set in advance on the mobile terminal 2. The updating time is a period of time when the time stamp that is encoded by the high-density two-dimensional code 4 is rewritten into a latest code for re-display every time the updating time elapses. For example, on the mobile terminal 2, the updating time can be set at 5 seconds, and the effective time limit can be set at 30 seconds. As a result, the reception PC 1 and the electronic chart system 6 can be prevented from being connected at an unintended timing.

At step S30, since the high-density two-dimensional code 4 is encoded in step with the time information on the time stamp, the shape of the high-density two-dimensional code 4 continues to change at all times.

At step S40, the system log-in authentication symbol can be used as an authentication symbol by temporarily being stopped changing its shape by tapping the display unit of the mobile terminal.

A stopping time of the authentication symbol that is temporarily stopped changing its shape can be controlled by setting it in advance in the two-dimensional symbol creating software.

At step S50, the authentication symbol that is temporarily stopped changing its shape is caused to face a high-density two-dimensional code authentication read scanner 5, so that the information of the high-density two-dimensional code 4 including the information of the time stamp is imaged, and the information so imaged is transmitted to the electronic chart system 6. The information of the high-density two-dimensional code 4 may be transmitted directly to the electronic chart system 6 by way of an appropriate network as illustrated in FIG. 1 or may be transmitted to the electronic chart system 6 by way of the reception PC 1.

At step S60, the electronic chart system 6 analyzes a sequence of the time stamp (for example, a data array or structure of the time stamp) from the transmitted high-density two-dimensional code information that includes the time stamp information and determines whether the high-density two-dimensional information is true or false. For example, if the time stamp that is analyzed falls within a range of a predetermined value, the electronic chart system 6 can determined that the information satisfies the condition at step S60 (the information is true).

At step S70, the electronic chart system 6 verifies the system connecting information (a connecting destination, a connection port, and a main access key) that is contained in the access that has passed through the analysis at step S60, and verifies whether the system connecting information matches the information recorded in advance.

At step S80, the electronic chart system 6 allows only the access that has passed through step S60 and step S70 to be logged in thereto, thereby permitting the information to access the electronic chart system 6.

At step S80, after having confirmed the permission for connection, the reception PC 1 enables the electronic chart system 6 to output the patient's electronic chart personal number that is recorded in advance, and the personal information including the address, name, contact telephone number, type of health insurance, health insurance card number, medical history (hypertension, diabetes, cancer myocardial infarction, cerebral infarction, and the like), nursing care insurance (the aged), allergy, tobacco, alcohol, family history (history of dieses or the like) of the patient, which are tagged (associated with the personal number).

Additionally, the details of a bank account of a person or a patient including an account balance can be recorded in the high-density two-dimensional code 4 that records the personal information, and the user can update the accumulated information by transmitting information to the database server that the user logs in to or can browse the information of the system through the mobile terminal 2.

When transmitting information, GPS position information can also be included in the information to be transmitted, and therefore, by determining on places where to transmit and receive information in advance and registering them in the electronic chart system, an unidentified connection or access can be blocked.

Further, the time limit is set for the display of a high-density two-dimensional code to be generated, so that the generated high-density two-dimensional code becomes invisible from the display when the set time limit has elapsed, whereby the authentication in the electronic chart system is also made impossible. Thus, the security at the time of personal authentication can be enhanced, whereby the method for logging in to the electronic chart system can be provided.

According to the present invention, the personal information of a patient for use for his or her electronic chart is the information that is authenticated at and passes through the hurdles (the time stamp, the scanner activated password, the time limit of the symbol) provided to prevent the leakage of the information that is protected in several ways from the specified mobile terminal, and the method for logging in to the system that secures the personal privacy information can be provided by the information (the connecting destination, the connection port, the main access key) for connecting to the electronic chart database server 6.

What is claimed is:

1. A method for logging in to into a system,
receiving by a reception PC personal information of a patient that is recorded by an input unit;
embedding an electronic chart personal number in the personal information of the patient by the reception PC, and recoding the personal information in a recording unit;
transmitting, by a transmission unit of the reception PC, the personal information to an electronic chart system by use of an information transmission unit based on data recorded by the input unit;
embedding, by a mobile terminal, a time stamp in information (a connecting destination, a connection port, a main access key) for connecting to the electronic chart system and generating an authentication high-density two-dimensional code encoding the information for connecting to the electronic chart system with the embedded time stamp;
reading by the authentication high-density two-dimensional code scanner the generated authentication high-density two-dimensional code;
transmitting the authentication high-density two dimensional code read by the authentication high-density two-dimensional code scanner to the electronic chart system, and
verifying, by the electronic chart system, whether the authentication high-density two-dimensional code matches a sequence of time stamp information of a symbol and satisfies a condition of the information (a connecting destination, a connection port, a main access key) for connecting to the electronic chart system, and outputs the personal information of the patient in the case where the condition is met.

2. The method for logging into a system according to claim 1, wherein the high-density two-dimensional code generated by the mobile terminal changes shape when encoded with the time stamp in synchronism with time information.

3. The method for logging into a system according to claim 1, wherein the high-density two-dimensional code generated by the mobile terminal is specialized in logging into the electronic chart system by encrypting a header portion.

4. The method for logging into a system according to claim 1, wherein the high-density two-dimensional code generated by the mobile terminal is made to be kept displayed within a time limit to be set and becomes invisible when the time limit set elapses.

5. The method for logging into a system according to claim 1, wherein positional information of the mobile terminal is registered in advance, whereby the electronic chart system authenticates only a connection request including the registered positional information and permits the connection request to connect thereto.

* * * * *